United States Patent [19]

Hasegawa et al.

[11] Patent Number: 4,795,444

[45] Date of Patent: Jan. 3, 1989

[54] SYRINGE

[75] Inventors: Kenji Hasegawa, Ibaraki; Kyaji Matsui, Kusatsu; Seiji Kita, Takatsuki; Seiichiro Kubo, Otsu; Seiichi Iida, Takatsuki, all of Japan

[73] Assignee: Sunstar Kabushiki Kaisha, Osaka, Japan

[21] Appl. No.: 41,488

[22] Filed: Apr. 23, 1987

[30] Foreign Application Priority Data

May 2, 1986 [JP] Japan .............................. 61-67318[U]
Mar. 16, 1987 [JP] Japan .............................. 62-38627[U]

[51] Int. Cl.⁴ ........................................... A61M 5/315
[52] U.S. Cl. .................................................. 604/218
[58] Field of Search ................. 604/218, 207, 89, 219, 604/221

[56] References Cited

U.S. PATENT DOCUMENTS

| | | | |
|---|---|---|---|
| 3,016,896 | 1/1962 | Van Sickle | 604/89 |
| 3,216,616 | 11/1965 | Blankenship, Jr. | 604/207 |
| 3,262,608 | 7/1966 | Macey | 604/218 X |
| 3,881,484 | 5/1975 | Gidcumb, Jr. | 604/89 |
| 3,882,866 | 5/1975 | Zackheim . | |
| 4,464,173 | 8/1984 | Tartaglia . | |

FOREIGN PATENT DOCUMENTS

| | | |
|---|---|---|
| 178158 | 3/1954 | Austria . |
| 0145922 | 6/1985 | European Pat. Off. . |
| 2178019 | 11/1973 | France . |
| 2543833 | 10/1984 | France . |
| 59-10985 | 4/1984 | Japan . |

*Primary Examiner*—John D. Yasko
*Attorney, Agent, or Firm*—Wegner & Bretschneider

[57] ABSTRACT

A syringe having a barrel fitted with a plunger and a nozzle in which the barrel comprises a hollow cylindrical portion and a tubular portion which is thinner than the cylindrical portion and connected to one end of the cylindrical portion, the other end of said cylindrical portion is an open end, and at least a part of the cylindrical portion adjacent to the open end has a diameter larger than that of one end of the plunger to be inserted in the barrel so that air present between the end of the plunger and the top surface of a medicament in the barrel can vent through the enlarged diameter part when the plunger is pushed into the barrel.

2 Claims, 3 Drawing Sheets

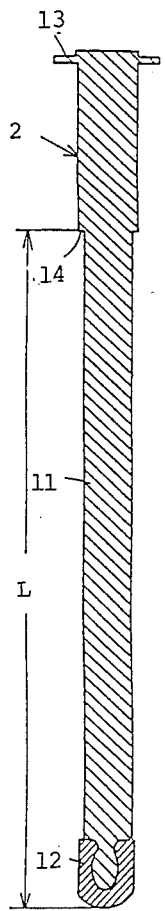
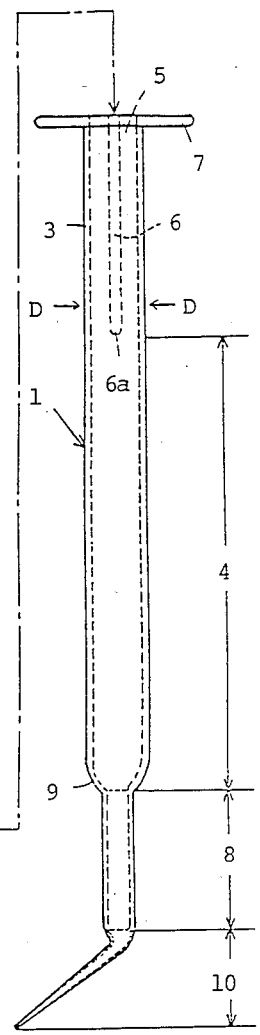
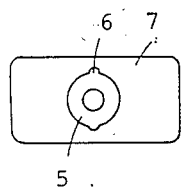
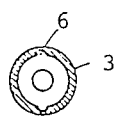
Fig. 1 (A)
Fig. 1 (B)
Fig. 1 (C)
Fig. 1 (D)

Fig. 2
Fig. 3 (A)
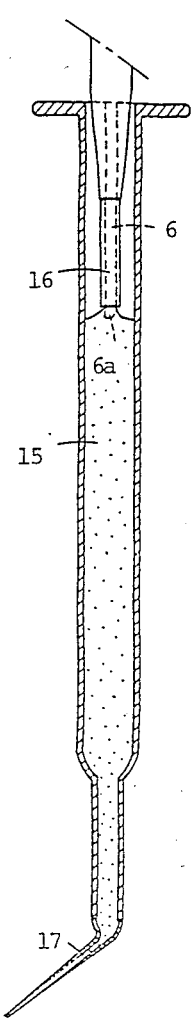
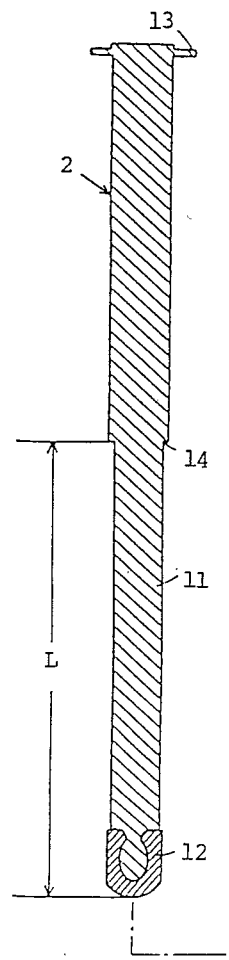
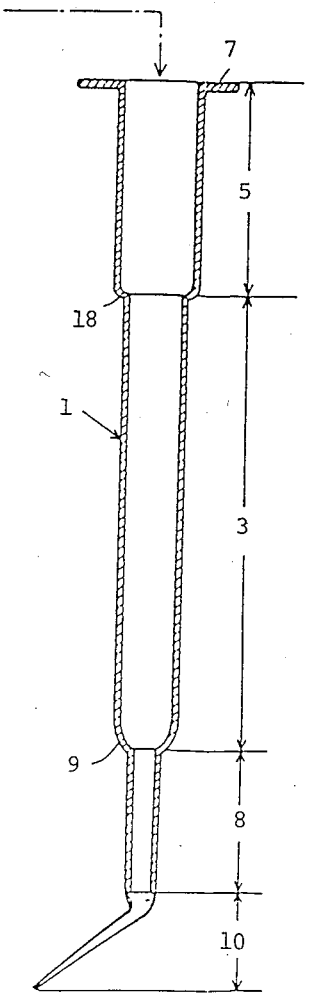
Fig. 3 (B)
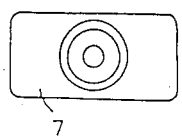

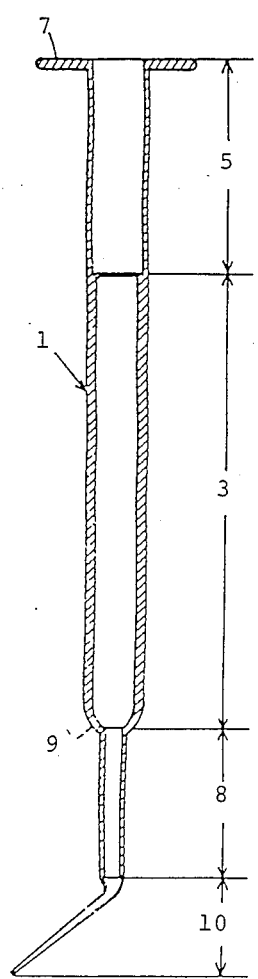
Fig. 4
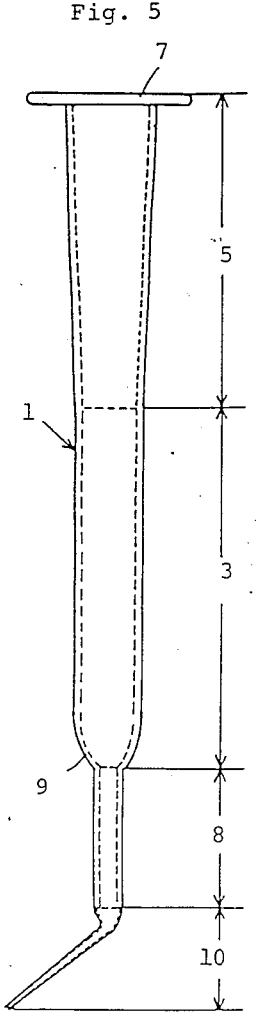
Fig. 5
Fig. 6
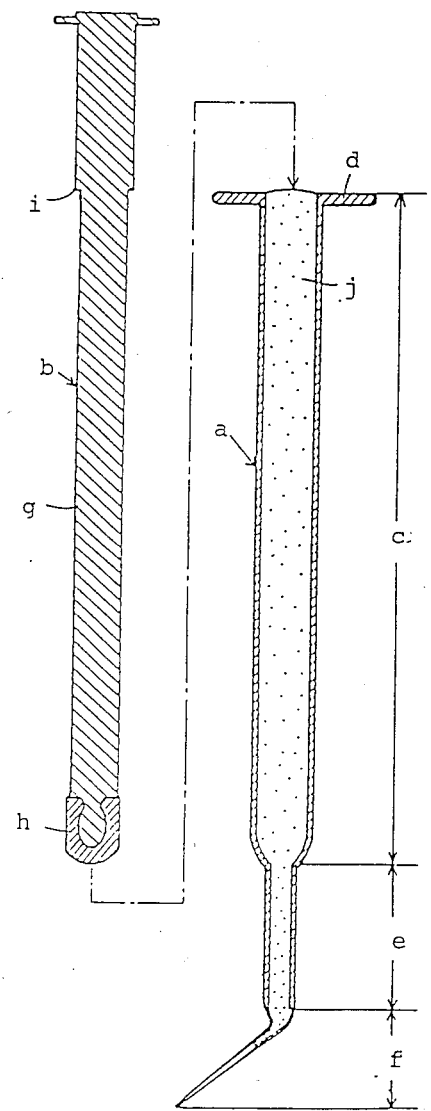

SYRINGE

FIELD OF THE INVENTION

The present invention relates to a syringe. More particularly, it relates to a syringe such as a dentist's syringe having good handling properties which can readily apply a medicament to a diseased part with minimum loss of the medicament.

BACKGROUND OF THE INVENTION

Hitherto, a syringe for applying a medicament to a limited diseased part such as that in the oral cavity has been known (see, for example, Japanese Design Publication Nos. 464190 and 681235) Such a syringe comprises a barrel fitted with a plunger and a nozzle. Usually, a barrel has a hollow cylindrical portion and a tubular portion which is thinner than the cylindrical portion and connected to one end of the cylindrical portion. The other end of the cylindrical portion is an open end and has a flange. The cylindrical portion may be slightly tapered from its open end to the tubular portion and the tubular portion is connected to the nozzle. The plunger has a gasket on one end of its piston rod to be pushed in the barrel through its open end. The outer diameter of the gasket is substantially the same as the inner diameter of the cylindrical portion. The other end of the plunger is pushed to insert the plunger into the barrel. A medicament is filled in the barrel and, when it is applied to the diseased part, the plunger is fully inserted into the barrel to push out the medicament through the nozzle toward the diseased part part. The plunger has a shoulder portion formed on a appropriate position of the side wall of the plunger and, as the plunger inserted into the barrel, the shoulder portion is brought into contact with the flange of the cylindrical portion to limit the insertion.

And, in order to fill a medicament having high viscosity into the barrel, it is filled through the open end of the barrel with a filler nozzle, while the barrel is set upright so that the open end is at the top thereof because it is difficult to suck the medicament into the barrel through the nozzle of the syringe. In this case, the filler nozzle tip is firstly located in the bottom of the barrel and then the filler nozzle is moved toward the open end, while filling of the medicament is continued with preventing inclusion of air. The medicament is filled up to tee level of the flange of the cylindrical portion. This filling manner is necessary to prevent inclusion of air between the gasket and the medicament when the plunger is pushed into the barrel.

However, in this case, since the medicament is filled up to the level of the flange of the cylindrical portion, the medicament is overflowed from the barrel when the plunger is pushed in the barrel to smear the flange and thereabout. Further, it is necessary that the plunger moves a certain distance toward the inside of the barrel to make the plunger in a self-supporting state prior to the use of the syringe for application of the medicament. In this case, a volume of the medicament corresponding to the movement of the gasket in the barrel is pushed out through the nozzle and discarded without utilizing it. This is uneconomic and, even if it can be recovered, it is very difficult to return it to the filler with maintaining an aseptic state.

Further, in the case of a dentist's syringe, the diseased part is located in the inner part of the oral cavity and therefore the barrel should have a certain length so that the nozzle reaches to the diseased part. Naturally, this rules the length of the plunger which is inserted into the barrel. That is, the plunger should also have a corresponding length. However, from the viewpoint of handling properties, it is preferred that the plunger has a relatively shorter length, and the requirement for making the plunger shorter is inconsistent with the requirement for making the barrel as long as possible. It has been requested to solve this inconsistent matter. And, even when the barrel is longer, the medicament should be also filled up to the level of the flange of the cylindrical portion to prevent inclusion of air, which makes the volume of the medicament to be filled much larger in comparison with that required for actual application. The excess amount of the medicament is discarded without utilization. This is uneconomic and, particularly, in the case that a syringe in which a medicament has been already filled is marketed, the excess amount of the medicament reflects the increase in the production cost of the syringe.

OBJECTS OF THE INVENTION

One object of the present invention is to provide an improved syringe, particularly, a dentist's syringe in which a medicament even having high viscosity can be readily filled.

Another object of the present invention is to provide an improved syringe having good handling properties which can readily apply a medicament to a diseased part with minimum loss of the medicament.

Still another object of the present invention is to provide a medicament containing improved syringe which can be marketed as it is.

These objects as well as other objects and advantages of the present invention will become apparent to those skilled in the art from the following description with reference to the accompanying drawings.

BRIEF EXPLANATION OF DRAWINGS

FIGS. 1 (A) to (D) illustrate a preferred embodiment of the syringe of the present invention and FIG. 1 (A) is a longitudinal section of the plunger. FIG. 1 (B) is a side view of the barrel and the nozzle. FIG. 1 (C) is a plan view of the barrel of FIG. 1 (B) and FIG. 1 (D) is a cross section taken along the line D—D in FIG. 1 (B).

FIG. 2 is a longitudinal section of the barrel as shown in FIG. 1 (B) for illustrating a filling manner of a medicament.

FIG. 3 shows another preferred embodiment of the syringe of the present invention and FIG. 3 (A) is a longitudinal section of both plunger and barrel. FIG. 3 (B) is a plan view of the barrel of FIG. 3 (A).

FIG. 4 is a longitudinal cross section of a barrel of still another preferred embodiment of the syringe of the present invention.

FIG. 5 is a longitudinal cross section of a barrel of still another preferred embodiment of the syringe of the present invention.

FIG. 6 is a longitudinal section of both plunder and barrel of a known syringe.

DETAILED EXPLANATION OF THE INVENTION

According to the present invention, there is provided a syringe having a barrel fitted with a plunger and a nozzle in which the barrel comprises a hollow cylindrical portion and a tubular portion which is thinner than the cylindrical portion and connected to one end of the cylindrical portion, the other end of said cylindrical portion is an open end, and at least a part of the cylindrical portion adjacent to the open end has a diameter larger than that of one end of the plunger to be inserted in the barrel so that air present between the end of the plunger and the top surface of a medicament in the barrel can vent through the enlarged diameter part when the plunger is pushed into the barrel.

In order to fill a medicament having high viscosity in the syringe of the present invention, the medicament is filled through the open end of the barrel with a filler nozzle, while the barrel is set upright so that the open end is at the top thereof. The filler nozzle tip is firstly located at the bottom of the barrel and then the filler nozzle is moved toward the open end, while filling of the medicament is continued with preventing inclusion of air. The medicament is filled up to the level about the enlarged diameter part at the cylindrical portion adjacent to the open end (hereinafter merely referred to as open end part). Then, one end of the plunger is pushed into the barrel through the open end to bring contact with the top surface of the medicament and further the plunder is pushed a certain distance into the barrel to complete filling of the medicament.

When the plunger is pushed into the barrel, air present between the end of the plunger and the top surface of the medicament vents through the enlarged diameter part to prevent inclusion of air. Further, the medicament overflowed by pushing the plunger into the barrel is kept in the enlarged diameter part to prevent smearing the flange. Furthermore, since the plunger can be inserted into the barrel beyond the enlarged diameter part from the beginning, the length of the plunger outside the barrel can make shorter in comparison with a known syringe, while maintaining a desired length of the barrel. This improves handling properties of the syringe. In addition, the amount of the medicament to be filled in the barrel can be controlled by adjusting the size and the length of the enlarged diameter part without change of the length of the barrel, which saves the production cost of the medicament containing syringe.

The shape and material of the syringe of the present invention are not limited to specific ones. They may be the same as those of a known syringe.

Further, a medicament to be filled in the syringe of the present invention is not limited to a specific one but, a paste composition having high viscosity is preferred in view of handling properties of the syringe of the present invention. Particularly, in the case of a dentist's syringe, it is preferred to use the aqueous minocycline paste as disclosed in European patent application publication No. 0 184 389 which comprises minocycline or a pharmaceutically acceptable salt thereof and a base composed of a polyhydric alcohol containing a magnesium compound.

Now referring to the drawings, the present invention is further illustrated in detail.

As shown in FIG. 6, a known syringe comprises a barrel (a) fitted with a plunger (b) and a nozzle (f). Usually, the barrel has a hollow cylindrical portion (c) and a tubular portion (e) which is thinner than the cylindrical portion and connected to one end of the cylindrical portion. The other end of the cylindrical portion is an open end and has a flange (d). The tubular portion is connected to the nozzle. The plunger has a gasket (h) on one end of its piston rod (g) to be pushed in the barrel through its open end The outer diameter of the gasket is about the same as the inner diameter of the cylindrical portion. The other end of the plunger is pushed to insert the plunger into the barrel. A medicament (j) is filled in the barrel and, when it is applied to a diseased part, the plunger is inserted into the barrel to push out the medicament through the nozzle toward the diseased part. The plunger has a shoulder portion (i) formed on a appropriate position of the side wall of the plunger and, as the plunger inserted into the barrel, the shoulder portion is brought into contact with the flange of the cylindrical portion to limit the insertion.

In this case, since the medicament (j) is filled up to the level of the flange (d) of the cylindrical portion (c), the medicament is overflowed from the barrel when the plunger is pushed in the barrel to smear the flange and thereabout. Further, although it is necessary to move the plunger a certain distance toward the inside of the barrel to make the plugger in a self-supporting state prior to use, a certain volume of the medicament corresponding to movement of the gasket in the barrel is pushed out through the nozzle and discarded without utilization. This is uneconomic and, even if it can be recovered, it is very difficult to return it to the filler with maintaining an aseptic state.

On the other hand the syringe of the present invention has the enlarged diameter part at the open end part of the barrel to solve these problems.

FIGS. 1 (A) to (D) show a preferred embodiment of the syringe of the present invention. This syringe comprises the barrel 1, the plunger 2 and the bent nozzle 10. As seen from FIG. 1 (B), the barrel is comprises a hollow cylindrical portion 3 and a tubular portion 8 which is thinner than the cylindrical portion and connected to one end of the cylindrical portion via a shoulder part 9. The other end of said cylindrical portion is an open end 5 and has a flange 7. The nozzle is connected to the portion 8.

As well seen from FIGS. 1 (C) and (D), there are two opposite longitudinally extending grooves 6 on the inside wall at the open end part of the cylindrical portion 3 which is served as the enlarged diameter part of the present invention to vent air present between the end of the plunger and the top surface of a medicament in the barrel. A medicament is filled in the part 4 of the cylindrical portion below the lower end 6a of the grooves. The position of the lower end 6a, that is, the length of the grooves 6 is determined by the required amount of a medicament to be filled and, by varying the length of the grooves 6, the amount of the medicament t be filled can be adjusted without changing the length of the barrel.

As seen from FIG. 1 (A), the plunger 2 has a piston rod 11 and a gasket 12 provided on one end of the piston rod. The gasket 12 is made of an elastic material the outer diameter of which has substantially the same as the inner diameter of the cylindrical portion 3 of the barrel. The other end of the plunger has a flange 13 to facilitate insertion of the plunger. Further, the plunger has a shoulder portion 14 which is brought into contact with the flange 7 of the cylindrical portion to limit the insertion. The position of the shoulder portion 14 is chosen in such a manner that the length (L) of the piston rod is substantially the same as the length of the cylindrical portion 3 so that the end of the gasket 12 can reach to the bottom of the cylindrical portion 3.

By the way, although this embodiment has two opposite grooves 6 on the inside wall at the open end part of the cylindrical portion, the syringe may have only one groove or more than two grooves. Further, in order to improve mechanical strength of the wall about the grooves, the outer surface of the wall corresponding to the grooves can be raised to form ribs.

Although FIG. 1 (B) does not show, the barrel may have a notch on an appropriate part of the inside wall adjacent to the open end part to prevent slipping out of the plunger after insertion. In addition, the nozzle may be a hollow needle for applying a liquid medicament such as a disinfectant solution or other medicaments having relatively low viscosity.

In the case of a medicament having relatively high viscosity, the medicament is filled as shown in FIG. 2.

That is, the medicament 15 is filled through the open end of the barrel with a filler nozzle, while the barrel is set upright so that the open end is at the top thereof. In this case, the filler nozzle tip 16 is firstly located at the bottom of the part 4 of the barrel and then the filler nozzle is moved toward the open end, while filling of the medicament is continued with preventing inclusion of air. The medicament is filled up to the level just above the lower end 6a of the grooves. The medicament 15 flows down into the nozzle 10 by its own weight but a little space 17 remains at the tip of the nozzle 10 because the medicament has relatively high viscosity.

In this state, the plunger 2 is pushed into the barrel through the open end thereof to bring the gasket 12 contact with the top surface of the medicament 15. In this case, the air present between the gasket 12 and the top surface of the medicament is vented through the grooves 6 to facilitate pushing the plunger into the barrel. Further, since the medicament is filled only up to the level just above the lower end 6a of the grooves, the plunger 12 is pushed into the barrel without overflow of the medicament to prevent smearing of the flange 7. On the other hand, as the plunger 2 is pushed into the barrel, the medicament is pushed down to fill the space 17 at the tip of the nozzle 10 and to remove the air in that space. Thus, the air in the barrel 1 is completely exhausted.

In the case of filling a medicament having much higher viscosity such as that in the form of a paste, a somewhat different filling manner is employed That is, in this case, the filler nozzle tip 16 is firstly located somewhat above the bottom of the part 4 and then the filler nozzle is moved toward the open end, while filling of the medicament is continued. The medicament 15 pushed out into the part 4 does not flow down due to high viscosity and a space containing air remains below the part 4. After filling, the plunger 2 is pushed to the top surface of the medicament to exhaust the air in the part 8 and the nozzle 10. According to this filling manner, it is possible to push down the top surface within a distance corresponding to the volume of the air remained below the part 4. Therefore, when a required amount of the medicament is small, that is, there is no need to fill the medicament within the part 4 entirely, such a manner further saves the amount of the medicament to be used. In addition, since air remains below the part 4, it is possible to push the plunger 2 a relatively larger distance into the barrel 1 to facilitate the control of pushing down of the plunger 2.

FIGS. 3 (A) and (B) show another preferred embodiment of the syringe of the present invention. This syringe also comprises the barrel 1, the plunger 2 and the bent nozzle 10. As seen from FIG. 3 (A), the barrel comprises a hollow cylindrical portion 3 and a tubular portion 8 which is thinner than the cylindrical portion and connected to one end of the cylindrical portion via a shoulder part 9. The other end of said cylindrical portion is connected to the open end portion 5 having a flange 7 via a shoulder part 18. The nozzle is connected to the portion 8.

The open end portion 5 is thicker than the cylindrical portion 3 and is served as the enlarged diameter part of the present invention to vent air present between the end of the plunger and the top surface of a medicament in the barrel. A medicament is filled in the cylindrical portion 3 up to the level of the shoulder part 18. The length of the cylindrical portion 3 is determined by the required amount of a medicament to be filled.

The plunger 2 is similar to that shown in FIG. 1 (A) and has a piston rod 11 and a gasket 12 provided on one end of the piston rod. The plunger has a shoulder portion 14 which is brought into contact with the shoulder part 18 to limit the insertion of the plunger. The position of the shoulder portion 14 is chosen in such a manner that the length (L) of the piston rod is substantially the same as the length of the cylindrical portion 3 so that the end of the gasket 12 can reach to the bottom of the cylindrical portion 3. Alternatively, the position of the shoulder portion 14 can be chosen in such a manner that the portion 14 is brought into contact with the flange 7 to limit the insertion of the plunger.

The medicament can be filled in this syringe according to the same manner as described above.

FIGS. 4 and 5 also show other preferred embodiments of the barrel of the syringe of the present invention.

In FIG. 4, like the syringe of FIG. 3 (A), the barrel 1 has the open end portion 5 which serves as the enlarged diameter part of the present invention. The inner diameter of the open end portion 5 is larger than that of the cylindrical portion 3, while the outer diameter of the former is the same as that of the latter.

In FIG. 5, the barrel 1 also has the open end portion 5 which serves as the enlarged diameter part of the present invention. The part 5 is tapered from the open end to the cylindrical portion 3.

The same filling manner can be employed in these embodiments.

After filling in the syringe of the present invention, the medicament can be immediately applied to a diseased part according to the same manner as in a known syringe, for example, by pushing the flange 13 of the plunger 2 with the thumb, while supporting the flange 7 with the forefinger and the middle finger. Alternatively, after filling the medicament in the syringe of the present invention, the medicament containing syringe can be marketed, for example, by closing the tip of the nozzle 10 with a cap or heat-sealing, subjecting the syringe to sterilization and then packing the syringe.

In the syringe of the present invention, by adjusting the size and the length of the enlarged diameter part, the length of the barrel can be appropriately determined regardless of the amount of the medicament to be filled. Therefore, for example, in the the case of applying the medicament to a diseased part in the oral cavity, it is possible to make the length of the barrel long to facilitate application of the medicament to the diseased part. Further, due to the presence of the enlarged diameter part, the length of the plunger outside the barrel can be made shorter without increase in the amount of the medicament to be discarded. This saves the amount of the medicament and improves handling properties of the syringe.

As described hereinabove, by providing the enlarged diameter part in which no medicament is filled to the open end part of the barrel according to the present invention, air present between the end of the plunger and the top surface of the medicament vents through it to prevent inclusion of air, which results in improvement of chemical stability of the medicament. Further, the medicament overflowed by pushing the plunger into the barrel is kept in the enlarged diameter part to prevent smearing the flange. Further, the amount of the medicament to be filled can be controlled by appropriately determining the size and length of the enlarged diameter part, which minimizes the loss of the medicament and saves the production cost. Furthermore, since the length of the barrel can be chosen regardless of the amount of the medicament, it can be determined mainly form the viewpoint of handling properties. In addition, the length of the plunger outside the barrel can make shorter by the length corresponding to that of the enlarged diameter part. This improves handling properties of the syringe.

The invention being thus described, it will be obvious that the same way be varied in many ways. Such modifications are not to be regarded as a departure from the spirit and scope of the present invention, and all such modifications are intended to be included within the scope of the following claims.

What is claimed is:

1. A dentist's syringe, comprising:
   (A) a barrel, said barrel comprising:
      (1) a hollow cylindrical portion having a first and a second end and an inner and an outer diameter, wherein a part of said cylindrical portion extending from said first end has an inner diameter which is larger than the inner diameter of the remainder of the cylindrical portion, and wherein the outer diameter of the cylindrical portion is essentially constant; and
      (2) a tubular portion of smaller diameter than said cylindrical portion, said tubular portion being connected to the second end of said cylindrical portion;
   (B) a nozzle connected to said tubular portion; and
   (C) a plunger which is insertable into said cylindrical portion so that air trapped between the plunger and medicament within said barrel can vent through a space formed between the plunger and the part of said cylindrical portion having a larger inner diameter.

2. A syringe according to claim 1, wherein medicament has been already filled in the barrel.

* * * * *